United States Patent [19]

Chandran et al.

[11] Patent Number: 5,632,976
[45] Date of Patent: May 27, 1997

[54] SOLUTION POLYMERIZATION OF VINYL MONOMERS WITH WATER SOLUBLE INITIATORS IN SUBSTANTIALLY NON-AQUEOUS MEDIA

[75] Inventors: Rama S. Chandran, Bound Brook; George Gallaway, Asbury, both of N.J.

[73] Assignee: National Starch and Chemical Investment Holding Corporation, Wilmington, Del.

[21] Appl. No.: 703,758

[22] Filed: Aug. 27, 1996

Related U.S. Application Data

[62] Division of Ser. No. 281,895, Jul. 28, 1994, Pat. No. 5,576,403.

[51] Int. Cl.$^6$ .................................. A61K 7/06
[52] U.S. Cl. .................................. 424/70.16
[58] Field of Search .................................. 424/70.16

[56] References Cited

U.S. PATENT DOCUMENTS

| | | | |
|---|---|---|---|
| 3,927,199 | 12/1975 | Micchelli et al. | 424/47 |
| 4,065,523 | 12/1977 | Hutton et al. | 260/885 |
| 4,898,677 | 2/1990 | Brase | 210/701 |
| 5,023,368 | 6/1991 | Leighton et al. | 560/195 |
| 5,055,503 | 10/1991 | Leake et al. | 524/30 |
| 5,066,749 | 11/1991 | Leighton et al. | 526/271 |

OTHER PUBLICATIONS

Research Disclosure, May 1984, pp. 232–233.
"Control of Particle Size in Dispersion Polymerization of Methyl Methacrylate", S. Shen, E. D. Sudol, and M. S. El-Aasser, Journal of Polymer Science: Part A: Polymer Chemistry, vol. 31, 1393–1402 (1993), John Wiley & Sons, Inc.

*Primary Examiner*—Joseph L. Schofer
*Assistant Examiner*—N. Sarofim
*Attorney, Agent, or Firm*—Ellen T. Dec

[57] ABSTRACT

In a process for the homogeneous polymerization of water insoluble polymers containing greater than 50% by weight of monomers selected from the group consisting of $C_1$–$C_{18}$ acrylate or methacrylate esters, N-substituted acryl or methacrylamides and mixtures thereof in substantially non-aqueous organic solutions, the improvement which comprises using as the polymerization initiator a water soluble initiator dissolved in sufficient amount of water to dissolve the initiator whereby the resultant polymer is characterized by lower residual monomer levels than are obtained using equivalent amounts of water-insoluble initiators.

3 Claims, No Drawings

SOLUTION POLYMERIZATION OF VINYL MONOMERS WITH WATER SOLUBLE INITIATORS IN SUBSTANTIALLY NON-AQUEOUS MEDIA

This application is a division of application Ser. No. 08/281,895, filed Jul. 28, 1994, now U.S. Pat. No. 5,576,403.

BACKGROUND OF THE INVENTION

Inorganic flee-radical initiators such as metal or ammonium salts of persulfate or other water soluble initiators such as redox systems are commonly employed in both aqueous solution, dispersion or emulsion polymerization of vinyl monomers. These inorganic initiators are relatively inexpensive and do not produce undesirable decomposition products compared with organic initiators commonly employed in vinyl free-radical polymerization.

Due to their insolubility in organic solvents such as alcohols, ketones, esters, hydrocarbons, etc., these water soluble initiators can not be used in such non-aqueous homogeneous (solution) polymerization processes. Non-aqueous solution free-radical polymerizations are therefore carried out with organic solvent soluble initiators such as peroxy esters of organic acids or organic azo initiators. The use of these initiators is often undesirable since the decomposition and reaction products of the organic initiators are toxic and/or cause undesirable odor in the final product which are used in personal products such as cosmetics.

SUMMARY OF THE INVENTION

We have found that water soluble compounds can be effectively used as initiators in substantially organic solvent media by incorporating a sufficient amount of water along with the organic solvent so as to dissolve the initiator and keep the monomers and polymer in solution throughout the polymerization process. The amount of water in the polymerization is below about 25 percent by weight of the total solution, preferably from 2 to 18% by weight so as to permit a homogeneous polymerization of water insoluble monomers and polymeric systems while keeping the initiator in solution.

The polymers prepared by this process have only sulfate (in case of persulfates) or non-hazardous and nonvolatile inorganics or organics as the initiator byproduct(s) and thus are devoid of the undesirable initiator decomposition products obtained with organic initiators.

Moreover, the use of the water soluble initiators provides an unexpected improvement in the efficiency of the reaction, resulting in higher conversion rates with substantially lower amounts of residual (unreacted) monomers, enabling the reaction to be carried out using substantially lower amounts of the initiator. Thus, this polymerization process using water soluble initiator in substantially organic media unexpectedly results in increased monomer conversions compared with many commonly employed organic initiators such as peroxy esters, and azo initiators used at equivalent molar concentrations without any undesirable initiator byproducts or loss of product performance.

DETAILED DESCRIPTION OF THE PREFERRED EMBODIMENT

The process of the present invention can be used to prepare virtually any water insoluble polymer in homogeneous form using conventional solution polymerization procedures in substantially non-aqueous media.

The homogeneous polymers prepared according to the invention generally contain substantial amounts, i.e., greater than about 50% by weight of $C_1$ to $C_{18}$ acrylate or methacrylate esters, or N-substituted acryl or methacrylamides or mixtures thereof.

One of the polymeric systems for which this procedure is most useful is the polymerization of film forming polymers to be used in hair fixing compositions. These polymers comprise moieties derived from (1) at least one comonomer which is an N-alkyl acrylamide or methacrylamide, (2) at least one acidic comonomer containing one or more available carboxyl groups, and (3) at least one copolymerizable comonomer.

The applicable N-substituted acrylamides or methacrylamides are substituted with alkyl radicals containing from 2 to 12 carbon atoms. Among the applicable acrylamides and methacrylamides are included N-ethyl acrylamide, N-tertiary-butyl acrylamide, N-n-octyl acrylamide, N-tertiary-octyl acrylamide, N-decyl acrylamide, N-dodecyl acrylamide, as well as the corresponding methacrylamides.

The acidic film forming comonomers containing at least one available carboxylic acid group including: acrylic acid, methacrylic acid, crotonic acid, itaconic acid, maleic acid, fumaric acid and the $C_1$–$C_4$ alkyl half esters of maleic and fumaric acids such, for example, as methyl hydrogen maleate and butyl hydrogen fumarate as well as any other acidic monomers which are capable of being copolymerized with the particular interpolymer system.

The acidic comonomers make it possible for the resultant copolymer to be neutralized by reaction with an appropriate base in order that it may ultimately exhibit the requisite water solubility. These acidic comonomers may be neutralized prior to their being incorporated into the ultimate hair fixing formulation thus permitting these formulations to be removed from the hair merely by rinsing with water. However, if such copolymers are not pre-neutralized in this manner, removal may still be readily effected by the application of an alkaline aqueous solution, for example, soap and water. The copolymerizable monomers used in these hair care formulations include the acrylic and methacrylic acid esters of aliphatic alcohols having from 1 to 12 carbon atoms such as methyl, ethyl, propyl, butyl, octyl and lauryl alcohols; hydroxyalkyl esters of acrylic and methacrylic acids such as hydroxypropyl acrylate and methacrylate, hydroxybutyl acrylate and methacrylate, hydroxystearyl acrylate and methacrylate and hydroxyethyl acrylate and methacrylate; alkyl ($C_1$–$C_4$) amino alkyl ($C_2$–$C_4$) esters of acrylic and methacrylic acids such as N,N'-diethylaminoethyl acrylate, tert-butylaminopropyl acrylate, N,N'-dimethylaminoethyl methacrylate, N-tert-butylaminoethyl methacrylate and the quaternization product of dimethylaminoethyl methacrylate and dimethyl sulfate, diethyl sulfate and the like; diacetone acrylamide; vinyl esters such as vinyl acetate and vinyl propionate; and styrene monomers such as styrene and alpha-methyl styrene.

The resultant polymer will contain from about 30 to 60% of the N-substituted acrylamide or methacrylamide, from 10 to 25% (and 12 to 18% preferably) of the acidic comonomer, and up to 55% of at least one copolymerizable comonomer; these percentages being based on the total weight of the interpolymer. Particularly useful are the polymers formed from the polymerization of 30 to 50% N-tert. octyl acrylamide, 12 to 20% acrylic or methacrylic acid, 32 to 38% methyl methacrylate, 2 to 10% hydroxypropyl acrylate and 2 to 10% of a ($C_1$–$C_4$) alkyl ($C_2$–$C_4$) aminoalkyl acrylate or methacrylate. These polymers and the use thereof are described in more detail in U.S. Pat. No. 3,927,199 issued Dec. 16, 1975 to Micchelli, et al.

The teachings of the invention are also useful in the homogeneous polymerization of $C_1$ to $C_{18}$ alkyl acrylates or methacrylates alone or copolymerized with vinyl ester or other acrylic polymers. Depending upon the components and amounts, these polymers may be prepared and adapted for a variety of end uses including as both pressure sensitive and non-pressure sensitive adhesive compositions.

Representative polymers made herein include substantial amounts, generally above about 70% by weight, alkyl esters of acrylic or methacrylic acid wherein the alkyl group contains from 1 to 18 carbon atoms, as well as polymers of vinyl acetate with vinyl ($C_3$ to $C_{10}$) ester polymers; copolymers of vinylidene chloride with alkyl esters of acrylic or methacrylic acid wherein said alkyl groups contain from 1 to 8 carbon atoms; and homopolymers of alkyl esters of acrylic or methacrylic acid wherein said alkyl groups contain from 1 to 8 carbon atoms.

The polymers may further comprise copolymerizable acrylic monomers other than alkyl esters of acrylic or methacrylic acid. Suitable acrylic monomers for use herein are the ethylenically unsaturated carboxylic acids: preferred acids are acrylic acid, and methacrylic acid, but other copolymerizable acids such as maleic acid, crotonic acid, itaconic acid, and fumaric acid can also be employed.

The polymer may also contain small amounts, of other copolymerizable comonomers including vinyl esters, hydroxyl containing monomers, mono or di-esters of unsaturated dicarboxylic acids, ethylenically unsaturated carboxylic acids and amines formed, for example by the reaction of propylene imine and a carboxyl-containing polymer, half esters of unsaturated dicarboxylic acids and the like.

The choice of solvents for the polymerization procedure described herein is governed by the solubility requirements of the monomers and the resulting interpolymers in that both the monomers and the resulting polymers should be soluble in the selected solvent or mixtures of solvents. The solvent or solvent mixture chosen must also be capable of dissolving a sufficient amount of water to keep the water soluble initiators in solution.

Examples of suitable solvents for the interpolymers include aromatic solvents such as toluene, xylene, etc. Suitable aliphatic solvents include esters such as ethyl acetate, propyl acetate, isopropyl acetate, butyl acetate, etc.; ketones such as methyl ethyl ketone, acetone, etc.; aliphatic hydrocarbons such as heptane, hexane, pentane, etc; $C_1$–$C_5$ alcohols such as methanol, propanol, t-butanol, etc. Especially useful are mixtures of the foregoing. As noted above, the solvent or solvent mixture chosen must also be capable of dissolving a sufficient amount of water to keep the inorganic initiators in solution. Examples of such solvent systems include pure solvents such as $C_1$–$C_5$ alcohols as well as mixtures of the $C_1$–$C_5$ alcohols with esters, ketones and aromatic hydrocarbons in appropriate ratios. Particularly preferred are solvent systems comprising 40 to 85% ethanol, 40 to 10% isopropyl acetate and 5 to 20% water.

Suitable as initiators herein are the water soluble initiators including thermal or heat activated initiators. Preferred heat activated initiators are the persulfates, such as ammonium persulfate, lithium persulfate, potassium persulfate and sodium persulfate.

The initiator is used in conventional ranges, generally about 0.5 mmol to 10 mmol per 100 g. of the monomer. In the case of thermal initiators, a range of 1 to 10 mmol is especially preferred. In use, the catalyst is dissolved in a small amount of water, i.e., less than 25% by weight of the total polymerization solution with the amount of water used being only enough to keep the initiator in solution.

It is further to be noted that only the specific monomers, solvent and initiator are present. This polymerization process of the present invention does not require the use of surfactants or protective colloids, nor is their presence desirable.

The polymers are prepared by organic solvent polymerization techniques involving in some cases delayed addition of monomer when there is a great disparity between reactivity ratios as for example between the reactivity ratios of vinyl acetate and acrylate monomers. The time interval for the delayed addition may range from about 60 to 600 minutes and longer. The techniques in general, involve the polymerization of the respective monomer mixtures in suitable organic solvents, the polymerization being initiated by the water soluble initiator.

The reaction is carried out using conventional solution polymerization procedures at temperatures of 50° to 100° C. for 2 to 10 hours or until a monomer conversion of about 99.9% or greater is achieved.

Depending on the polymeric composition and the desired end use, the polymer may be used neat or may be dissolved in additional solvent. In the case of polymers for hair care uses, the polymer may be partially neutralized prior to formulation into the ultimate hair fixing formulation thus permitting them to be removed from the hair merely by rinsing with water. This may be accomplished by reacting the polymer, in the form of a solution in an organic solvent, with or without added water, with a concentration of an alkaline reagent (neutralizing agent) which is equivalent on a molar basis to a minimum of about 50% of the available carboxyl groups present on the polymer. Applicable alkaline materials which may be utilized in this manner include: sodium and potassium hydroxide; ammonia; primary, secondary and tertiary amines; alkanolamines; and, hydroxyamines such as 2-amino-2-methyl-propanol and 2-amino-2-methyl-1,3-propanediol. However, if such polymers are not pre-neutralized in this manner, their eventual removal may still be readily effected by the application of weak alkaline aqueous solution, e.g., soap and water.

In utilizing the polymers in the preparation of aerosol hair sprays, the other essential ingredients which must be admixed therewith are a solvent and a propellant, although in some instances the propellant will serve both the latter functions. The preferred solvents are alcohols such as ethanol and isopropanol. In addition to their solubility properties, the prime advantages of these solvents are their ability to dry quickly, their minimal effect on the metal containers ordinarily utilized for these pressurized aerosol formulations and their accepted use in cosmetic applications. Other solvents which may be used include methylene chloride and 1,1,1-trichloromethane, etc.

Various types of aerosol propellants are well known to those skilled in the art. Thus, the commonly used propellants include trichlorofluoromethane, dichlorodifluoromethane, isobutane and propane, etc., as well as mixtures of the latter propellants. These propellants am readily compatible with the binder-solvent solutions utilized in this invention.

With regard to proportions, the final hair spray formulations typically contain the polymeric binder in a concentration ranging from about 0.25 to 7%, by weight; the solvent in a concentration ranging from about 8 to 90%, by weight; and the propellant concentration ranging from 10 to 85%, by weight. The latter proportion should, however, be considered as being merely illustrative inasmuch as it may well be possible to prepare operable formulations having concentrations of components which fall outside the above suggested ranges.

In addition, it should be noted that the unique film forming polymers of this invention are equally effective when utilized in hair setting lotions, which usually consist of a solution (or dispersion) of the polymer in a suitable organic solvent, such as alcohol, together with water. Such lotions may be directly applied to the hair or they maybe sprayed thereon utilizing conventional spray nozzles. The application of such lotions may take place prior to, during, or after the desired hair style has been achieved.

The latter hair lotions are prepared by merely admixing the film forming polymer with the selected solvent, such solvents usually comprising a mixture, with water, of an alcohol such as ethanol or isopropanol. With regard to proportions, the lotions typically contain from about 0.5 to 7%, by weight, of the polymeric binder, while any desired ratio of alcohol to water in the solvent system may be utilized therein. An all alcohol system may also be used in some cases.

Optional additives may be incorporated into the hair fixing formulations of this invention in order to modify certain properties thereof. Among these additives may be included: plasticizers such as glycols, phthalate esters and glycerine; silicones; emollients, lubricants and penetrants such as lanolin compounds, protein hydrolyzates and other protein derivatives, ethylene oxide adducts, and polyoxyethylene cholesterol; U.V. absorbers; dyes and other colorants; and perfumes.

EXAMPLE I

A polymer suitable for hair care uses was prepared as follows:

|  | MATERIAL | PARTS |
| --- | --- | --- |
| MONOMER MIX A | t-Octyl Acrylamide-60% EtOH | 66.7 |
|  | Acrylic Acid | 16. |
|  | Methyl Methacrylate | 35. |
|  | t-butylaminoethyl methacrylate | 4. |
|  | Hydroxypropyl Methacrylate | 5. |
| B | Sodium Persulfate | 0.10 |
|  | Water | 2.2 |
|  | Ethyl Alcohol | 13.8 |
|  | Monomer Mix A | 25. |
| C | Monomer Mix A | 101.7 |

-continued

|  | MATERIAL | PARTS |
| --- | --- | --- |
| D | Sodium Persulfate | 0.3 |
|  | Water | 7.5 |
|  | Ethyl Alcohol | 15. |
| E | Isopropyl Acetate | 30 |

Prepare monomer mix "A". Heat initial charge "B" to reflux (~82° C.) and hold at reflux for five minutes. Start monomer slow add "C" uniformly over three hours and catalyst slow add "D" over five hours. Hold at reflux for one hour after catalyst slow add "D" is complete. Cool reactor contents, add dilution solvent E: and mix for thirty minutes.

The reactor contents were adjusted to 60° to 70° C. The polymer was precipitated and recovered by distillation and filtration. The resultant polymer, in the form of pearls, was forced air oven dried overnight at 60° C.

This sample was designated Sample 4, Table I (a duplicate was prepared and designated Sample Other samples were prepared using the procedure described above but varying the type and/or amount of the initiator. The initiators and amounts are indicated in Table I.

The procedure was repeated using various amounts of sodium persulfate (SPS). For comparison, samples were also prepared using conventional water insoluble initiators including benzoyl peroxide (BPO), t-amyl peroxypivalate (t-APP) and 2,2-azobis(2-methylbutane-nitrile) (V-67 supplied by DuPont). The samples, in the form of polymer pearls were analyzed for residual monomer content.

As the results presented in Table I show, the samples prepared with the sodium persulfate contained only one-tenth the residual level of t-octyl acrylamide or acrylic acid and substantially lower total monomer residuals as compared with comparable amounts of the conventionally used water insoluble polymers.

TABLE I

|  | SPS | | | | | BPO | | t-APP | | | V-67 | | | |
| --- | --- | --- | --- | --- | --- | --- | --- | --- | --- | --- | --- | --- | --- | --- |
| Sample | 1 | 2 | 3 | 4 | 5 | 6 | 7 | 8 | 9 | 10 | 11 | 12 | 13 | 14 |
| Parts* | 1.67 | 1.13 | 0.56 | 0.40 | 0.40 | 1.70 | 1.70 | 1.70 | 1.32 | 1.10 | 0.60 | 1.35 | 1.35 | 1.35 |
| m m Initiator* | 7 | 4.75 | 2.35 | 1.68 | 1.68 | 7. | 7. | 7. | 7. | 5.9 | 3.2 | 7. | 7. | 7. |
| Type Initiator | Sod Per | Sod Per | Sod Per | Sod Per | Sod Per | BPO | BPO | BPO | t-APP | t-APP | t-APP | V-67 | V-67 | V-67 |
| Scale | 2L | 2 | 2 | 2 | 2 | 2L | 2L | 2L | 5 | 2 | 2 | 2L | 5L | 5L |
| % Vol. | 2 | 2 | 2 | 2 | 2 | 1.6 | 2 | 1.62 | 1.1 | 1.3 | 1.2 | 2.2 | 2.2 | 2 |
| Acidity meq/g | 2.05 | 2.01 | 1.97 | 2 | 1.98 | 2.05 | 1.96 | 1.97 | 1.95 | 1.92 | 1.95 | 1.87 | 2.02 | 2 |
| I. V. (Etoh) | 0.26 | 0.26 | 0.38 | 0.4 | 0.46 | 0.33 | 0.32 | 0.31 | 0.32 | 0.33 | 0.34 | 0.31 | 0.32 | 0.3 |
| Residuals: ppm | | | | | | | | | | | | | | |

TABLE I-continued

| | SPS | | | | | BPO | | t-APP | | V-67 | | | |
|---|---|---|---|---|---|---|---|---|---|---|---|---|---|
| Sample | 1 | 2 | 3 | 4 | 5 | 6 | 7 | 8 | 9 | 10 | 11 | 12 | 13 | 14 |
| (Pearls) | | | | | | | | | | | | | | |
| Acrylic Acid | 110 | 115 | 120 | 95 | 122 | 84 | 1015 | 110 | 295 | 117 | 575 | 1325 | 80 | 77 |
| HPMA | <10 | <10 | <10 | <10 | <10 | 15 | <50 | <25 | 30 | 28 | 46 | <50 | <20 | <20 |
| MMA | <10 | <50 | <50 | <50 | <50 | <50 | <60 | <50 | <10 | <10 | <10 | <60 | <20 | <20 |
| t-BAEM | 144 | 45 | 74 | 81 | 82 | 26 | <50 | <50 | <10 | <10 | <10 | <50 | 62 | <20 |
| t-OA | <10 | 20 | 40 | 86 | 71 | 430 | 640 | 630 | 165 | 175 | 1300 | 470 | 113 | 306 |
| TOTAL | 284 | 240 | 294 | 322 | 335 | 605 | 1815. | 865 | 510. | 340 | 1941. | 1955 | 295 | 443 |

*based on 100 parts total monomer

EXAMPLE II

In a second series of tests, 7 m. moles of various other water insoluble initiators including 1,1-di-(t- butylperoxy) cyclohexane (t-BPC), t-amyperoxy acetate (t-APA), t-amylperoxy-2-ethylhexanoate (t-APO), 1,1-azobis (cyclohexane-1 -carbonitrile (V-40), dimethyl 2,2-azobisisobutyrate (V-601) and t- amylperoxpivalate (t-APP) were used to prepare polymers as described in Example I. The resultant polymers were analyzed for residual monomer content. The results of the testing, together with the results of the testing for comparable levels of the various initiators used in Example I are presented in Table II.

TABLE II

| SAMPLE | TYPE INIT. | t-OA | MMA | AA |
|---|---|---|---|---|
| 4 | Sodium Persulfate | <10 | 92 | <20 |
| 7 | BP | 640 | <60 | 1015 |
| 8 | BP | 630 | <50 | 110 |
| 12 | V-67 | 470 | <60 | 1325 |
| 13 | V-67 | 113 | <20 | 80 |
| 15 | t-APO | 36 | <10 | 849 |
| 16 | t-BPC | 531 | 264 | 2007 |
| 17 | t-APP | 1141 | <10 | 2565 |
| 18 | t-APA | 8749 | <10 | 1543 |
| 19 | V-40 | 645 | 65 | 200 |
| 20 | V-601 | 100 | <50 | 280 |

Again, the results show that the samples prepared with the water soluble initiators contained only one-tenth the residual level of t-octyl acrylamide or acrylic acid and substantially lower monomer residuals as compared with comparable amounts of the conventionally used water insoluble initiators

EXAMPLE III

The samples designated 3, 5, 7 and 13 were formulated into hair care products and compared for curl retention, as well as for other hair related properties using standard evaluation procedures. The results of the tests confirmed that the sodium persulfate initiated samples provided equal or better hair care (tactile) performance properties. Moreover, the sodium persulfate initiated samples also exhibited a substantially lower odor profile.

TABLE III

| | HIGH HUMIDITY CURL RETENTION 90% RELATIVE HUMIDITY 5% ANHYDROUS, NON-AEROSOLS | | | | | | | | |
|---|---|---|---|---|---|---|---|---|---|
| SAMPLE | 15 MIN | 30 MIN | 60 MIN | 90 MIN | 2 HRS | 3 HRS | 4 HRS | 5 HRS | 24 HRS |
| 5 | 99.38 | 96.94 | 94.53 | 92.71 | 92.71 | 90.85 | 90.24 | 89.62 | 86.53 |
| 3 | 98.25 | 94.12 | 90.5 | 87.41 | 86.82 | 81.28 | 80.11 | 80.11 | 76.43 |
| 13 | 96.83 | 85.45 | 81.01 | 77.78 | 77.13 | 74.59 | 73.28 | 72.04 | 68.81 |
| 7 | 98.21 | 90.93 | 85.46 | 83.03 | 82.41 | 80.04 | 79.39 | 78.77 | 75.72 |

TABLE IV

| | Statistically Comparable @ 95% Confidence SUBJECTIVE PROPERTIES (SAMPLE 3 VS. 7) 5% ANHYDROUS NON-AEROSOLS | | | | |
|---|---|---|---|---|---|
| SAMPLE | GLOSS | STIFFNESS | DRY COMB | FLAKE | ANTI-STAT |
| 3 | = | + | = | − | = |

− Inferior
= Equivalent
+ Superior

TABLE V

ODOR TEST
5% ANHYDROUS CONCENTRATIONS

| PANEL | SAMPLE 3 | SAMPLE 7 |
|---|---|---|
| 1 | | X |
| 2 | X | |
| 3 | | X |
| 4 | | X |
| 5 | | X |
| 6 | | X |
| 7 | X | |
| 8 | X | |

X = More offensive odor

Similar results would be obtaining using the water soluble persulfate initiators in the homogeneous polymerization of adhesive solutions containing substantial amounts of alkyl esters of acrylic or methacrylic acid or the like.

In summary, the process of the invention allows the use of inexpensive water soluble initiators to obtain much cleaner polymer products. This simplifies or eliminates purification of the final polymer from undesirable or hazardous components such as monomer residuals and initiator byproducts. Furthermore, the higher efficiencies of the water soluble compared with the organic initiators allows for use of much smaller amounts of the inexpensive water soluble initiator to obtain the desired product.

We claim:

1. A hair fixing composition containing low residual levels of residual monomer, the composition comprising a solvent selected from a group consisting of 1,1,1-trichloromethane, methylene chloride, ethanol, isopropanol, and water, and from 0.25 to 7%, by weight, of an interpolymer of 30 to 60% of a comonomer selected from the group consisting of N-alkyl acrylamide and N-alkyl methacrylamide wherein the alkyl group hereof contains from 2 to 12 carbon atoms; 12 to 18% of an acidic copolymerizable comonomer selected from the group consisting of acrylic acid, methacrylic acid, crotonic acid, itaconic acid, maleic acid, fumaric acid, and the ($C_1$–$C_4$) alkyl half esters of maleic and fumaric acids; and 20 to 55% of at least one copolymerizable comonomer selected from the group consisting of ($C_1$–$C_{12}$) alkyl acrylates, ($C_1$–$C_{12}$) alkyl methacrylates, ($C_2$–$C_4$) hydroxyalkyl acrylates, hydroxystearyl acrylate, hydroxyalkyl methacrylates, hydroxystearyl methacrylate, ($C_1$–$C_4$) alkyl ($C_2$–$C_4$) amino alkyl acrylates, ($C_2$–$C_4$)alkyl ($c_2$–$C_4$) aminoalkyl methacrylates, vinyl acetate, vinyl propionate, diacetone acrylamide, styrene, and alpha-methyl styrene; said interpolymer being sufficiently neutralized with an alkaline reagent to effect its solubility in water, wherein said polymer is prepared in homogeneous form in the presence of an organic solvent using, the solvent containing at least 40% ethanol as the polymerization initiator, a water soluble initiator in sufficient water to dissolve the initiator, the amount of water comprising 5 to 25% by weight of the total solvent.

2. The hair fixing composition of claim 1, wherein from 50 to 100% of the available carboxyl groups of the interpolymer are neutralized with an alkaline reagent.

3. A hair fixing composition of claim 1 wherein the polymer is formed from the polymerization of 30 to 50% N-tert octyl acrylamide, 12 to 18% acrylic or methacrylic acid, 32 to 38% methyl methacrylate, 2 to 10% hydroxypropyl acrylate and 2 to 10% of a ($C_1$–$C_4$)alkyl ($C_2$–$C_4$) aminoalkyl acrylate or methacrylate.

* * * * *